United States Patent
Kals

(10) Patent No.: US 11,077,302 B2
(45) Date of Patent: Aug. 3, 2021

(54) FAST OBJECTIVE FITTING MEASUREMENTS FOR COCHLEAR IMPLANTS

(71) Applicant: MED-EL Elektromedizinische Geraete GmbH, Innsbruck (AT)

(72) Inventor: Mathias Kals, Grinzens (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 113 days.

(21) Appl. No.: 16/488,815

(22) PCT Filed: Feb. 23, 2018

(86) PCT No.: PCT/US2018/019374
§ 371 (c)(1),
(2) Date: Aug. 26, 2019

(87) PCT Pub. No.: WO2018/160450
PCT Pub. Date: Sep. 7, 2018

(65) Prior Publication Data
US 2020/0030605 A1 Jan. 30, 2020

Related U.S. Application Data

(60) Provisional application No. 62/464,521, filed on Feb. 28, 2017.

(51) Int. Cl.
*A61N 1/36* (2006.01)
*A61N 1/05* (2006.01)
*H04R 25/00* (2006.01)

(52) U.S. Cl.
CPC ....... *A61N 1/36039* (2017.08); *A61N 1/0541* (2013.01); *H04R 25/70* (2013.01); *H04R 2225/67* (2013.01)

(58) Field of Classification Search
CPC .. A61N 1/36039; A61N 1/0541; H04R 25/70; H04R 2225/67
See application file for complete search history.

(56) References Cited

U.S. PATENT DOCUMENTS

| 6,415,185 B1 | 7/2002 | Maltan |
| 7,043,303 B1 | 5/2006 | Overstreet |

(Continued)

OTHER PUBLICATIONS

European Patent Office, Extended European Search Report, Application No. 18760391.5, dated Dec. 4, 2020, 7 pages.

(Continued)

*Primary Examiner* — Catherine M Voorhees
(74) *Attorney, Agent, or Firm* — Sunstein LLP

(57) ABSTRACT

A fitting system is described for fitting electrode contacts of cochlear implant electrode array implanted in a cochlea of an implanted patient. A test stimulation generator delivers to at least one of the electrode contacts a test stimulation sequence at a variable charge level and a variable stimulation rate over time, wherein the charge level and stimulation rate are inversely related as a function of a defined loudness percept by the implanted patient to the test stimulation sequence. A response measurement module obtains objective response measurements of auditory neural tissues of the implanted patient that are affected by the test stimulation sequence. A fit mapping module defines a patient-specific fit map for the electrode contacts of cochlear implant electrode array based on the objective response measurements.

22 Claims, 6 Drawing Sheets

(56) References Cited

U.S. PATENT DOCUMENTS

| | | | |
|---|---|---|---|
| 9,232,327 B2* | 1/2016 | Smith | H04R 25/552 |
| 2009/0259277 A1 | 10/2009 | Cornejo Cruz et al. | |
| 2011/0077712 A1* | 3/2011 | Killian | A61N 1/36038 |
| | | | 607/57 |
| 2011/0082521 A1 | 4/2011 | Botros et al. | |
| 2012/0065705 A1* | 3/2012 | Kals | A61N 1/36039 |
| | | | 607/57 |
| 2015/0018897 A1 | 1/2015 | Laudanski et al. | |
| 2016/0199642 A1* | 7/2016 | Schwarz | A61N 1/36039 |
| | | | 607/57 |

OTHER PUBLICATIONS

International Searching Authority/US, International Search Report and the Written Opinion of the International Searching Authority, Application No. PCT/US2018/019374, dated Apr. 27, 2018, 15 pages.

\* cited by examiner

FAST OBJECTIVE FITTING MEASUREMENTS FOR COCHLEAR IMPLANTS

CROSS-REFERENCE TO RELATED APPLICATIONS

This application is a U.S. national phase entry under 35 USC § 371 of Patent Cooperation Treaty Application No. PCT/US2018/019374 filed Feb. 23, 2018, which in turn claims priority from U.S. Provisional Patent Application 62/464,521, filed Feb. 28, 2017, the disclosures of which are incorporated herein by reference in their entirety.

TECHNICAL FIELD

The present invention relates to hearing implant systems, and more specifically, to custom fitting of hearing implant systems such as cochlear implants.

BACKGROUND ART

A normal ear transmits sounds as shown in FIG. 1 through the outer ear 101 to the tympanic membrane (eardrum) 102, which vibrates the ossicles of the middle ear 103 (malleus, incus, and stapes). The stapes footplate is positioned in the oval window 106 that forms an interface to the fluid filled inner ear (the cochlea) 104. Movement of the stapes generates a pressure wave in the cochlea 104 that stimulates the sensory cells of the auditory system (hair cells). The cochlea 104 is a long narrow duct wound spirally around its central axis (called the modiolus) for approximately two and a half turns. The cochlea 104 includes an upper channel known as the scala vestibuli, a middle channel known as the scala media and a lower channel known as the scala tympani. The hair cells connect to the spiral ganglion cells of the cochlear nerve 105 that reside in the modiolus. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. The electrode array 110 includes multiple electrode contacts 112 (also referred to as electrode channels) on its surface that provide selective stimulation of the cochlea 104.

A relatively small number of electrode channels are each associated with relatively broad frequency bands, with each electrode contact 112 addressing a group of neurons with an electric stimulation pulse having a charge that is derived from the instantaneous amplitude of the signal envelope within that frequency band. Current cochlear implant coding strategies map the different sound frequency channels onto different locations within the cochlea. FIG. 2 shows one example of the processing of a signal using the cochlear implant stimulation (CIS) stimulation strategy. The top of FIG. 2 shows the sound pressure characteristics of a spoken "A" (/ay/) at a sound level of 67.2 dB. The middle waveform in FIG. 2 shows a normal healthy auditory system response. The bottom waveform in FIG. 2 shows a neural response of the auditory nerve fibers under CIS stimulation.

FIG. 3 shows various functional blocks in a signal processing arrangement for producing electrode stimulation signals to electrode contacts in an implanted cochlear implant array according to a typical hearing implant system. A pseudo code example of such an arrangement can be set forth as:

Input Signal Preprocessing:
    BandPassFilter (input_sound, band_pass_signals)
    Envelope Extraction:
    BandPassEnvelope (band_pass_signals, band_pass_envelopes)
    Stimulation Timing Generation:
    TimingGenerate (band_pass_signals, stim_timing)
    Pulse Generation:
    PulseGenerate (band_pass_envelopes, stim_timing, out_pulses)

The details of such an arrangement are set forth in the following discussion.

In the signal processing arrangement shown in FIG. 3, the initial input sound signal is produced by one or more sensing microphones, which may be omnidirectional and/or directional. Preprocessor Filter Bank 301 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as and without limitation automatic gain control (AGC) and/or noise reduction and/or wind noise reduction and/or beamforming and other well-known signal enhancement functions. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 3011; incorporated herein by reference in its entirety.

The band pass signals $U_1$ to $U_K$ (which can also be thought of as electrode channels) are output to a Stimulation Timer 306 that includes an Envelope Detector 302 and Fine Structure Detector 303. The Envelope Detector 302 extracts characteristic envelope signals outputs $Y_1, \ldots, Y_K$ that represent the channel-specific band pass envelopes. The envelope extraction can be represented by $Y_k = LP(|U_k|)$, where |.| denotes the absolute value and LP(.) is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

The Fine Structure Detector 303 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_k$ can be assumed to be real valued signals, so in the specific case of an analytic orthogonal filter bank, the Fine Structure Detector 303 considers only the real valued part of $U_k$. The Fine Structure Detector 303 is formed of K independent, equally-structured parallel sub-modules.

The extracted band-pass signal envelopes $Y_1, \ldots, Y_K$ from the Envelope Detector 302, and the stimulation timing signals $X_1, \ldots, X_K$ from the Fine Structure Detector 303 are output from the Stimulation Timer 306 to a Pulse Generator 304 that produces the electrode stimulation signals Z for the electrode contacts in the implanted electrode array 305. The Pulse Generator 304 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
Pulse Rate
Number of fine structure channels
Compression
Parameters of frequency→electrode mapping
Parameters describing the electrical field distribution These patient-specific operating parameters are saved in a file referred to as a fit map. A given system may have multiple patient-specific fit maps for different listening environments; for example, there may be one fit map for a quiet environment and a different fit map for a noisy environment. The better the fit map, the more closely the hearing experience from the electrical stimulation signals resembles the natural acoustic hearing experience of unimpaired individuals.

One common method for fit adjustment is to behaviorally find the threshold (THR) and most comfortable loudness (MCL) value for each separate electrode contact. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL or THR is reached.

One approach for an objective measurement of MCLs and THRs is based on the measurement of the ECAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the superposition of single neural responses at the outside of the axon membranes. The amplitude of the ECAP at the measurement position is typically in the ranges of μV. When performing objective measurements such as ECAP measurements in existing cochlear implant systems, usually each electrode contact of the implantable electrode array is scanned separately, increasing the stimulation signal current on an electrode contact in steps from zero or a very low level until an ECAP response is detected. Other objective measurement approaches are also known, such as electrically evoked stapedius reflex thresholds (eSRT).

Once the fit parameters such as MCL and THR are initially established based on objective measurements, then an audiologist can further fine tune the fit map based on their experience and any available subjective feedback from the individual patient to modify the existing fit map by scaling, tilting, smoothing, or changing the shape of the fit map. However, the fitting audiologist needs to have many years of clinical experience and the fitting process can be quite time consuming. It is not trivial to test even some of the many possible adjustment combinations. In addition, patient feedback is not always available; for example, when the patient is a small child.

When developing a patient-specific fit map based on objective measurements such as ECAPs, the ECAP thresholds ($ECAP_{thrs}$) are typically audible to the implanted patient. On average, $ECAP_{thrs}$ are around 60% of the electric dynamic range. To exclude refractory effects, ECAP measurements are typically performed at fixed stimulation rates ≤100 pps. But it can happen that the patient-specific MCL can be exceeded before the $ECAP_{thrs}$ can be found.

Consequently, measuring the amplitude growth function (AGF) of the ECAP measurements can be very limited in awake patients—the ECAP measurement must be stopped manually when MCL is reached before the $ECAP_{thrs}$ is found. In sedated patients, measurements independent of MCL can be performed, but the resulting ECAPs are than different from those measured when the patient is awake.

SUMMARY

Embodiments of the present invention are directed to arrangements for fitting electrode contacts of a cochlear implant electrode array implanted in a cochlea of an implanted patient. A test stimulation generator delivers to at least one of the electrode contacts a test stimulation sequence at a variable charge level and a variable stimulation rate over time, wherein the charge level and stimulation rate are inversely related as a function of a defined loudness percept by the implanted patient to the test stimulation sequence. A response measurement module obtains objective response measurements of auditory neural tissues of the implanted patient that are affected by the test stimulation sequence. A fit mapping module defines a patient-specific fit map for the electrode contacts of cochlear implant electrode array based on the objective response measurements.

In specific embodiments, the response measurement module may be configured to obtain objective response measurements that include electrically evoked compound action potential (ECAP) measurements such as ECAP threshold measurements. The defined loudness percept used by the test stimulation generator may be based on a patient-specific Maximum Comfortable Loudness (MCL). The function of a defined loudness percept used by the test stimulation generator may represent a scaled product of an exponential charge amplitude factor and an exponential stimulus rate factor. The test stimulation generator may be configured to deliver a test stimulation sequence to a plurality of the electrode contacts; for example, to each of the electrode contacts.

Embodiments of the present invention also include a cochlear implant system fit to an implanted patient using any of the above methods.

DETAILED DESCRIPTION

Embodiments of the present invention are directed to cochlear implant fitting arrangements that produce a patient-specific fit map more quickly than with existing approaches without undesirably elevating the risk of overstimulation (without exceeding MCL).

Figure 1:
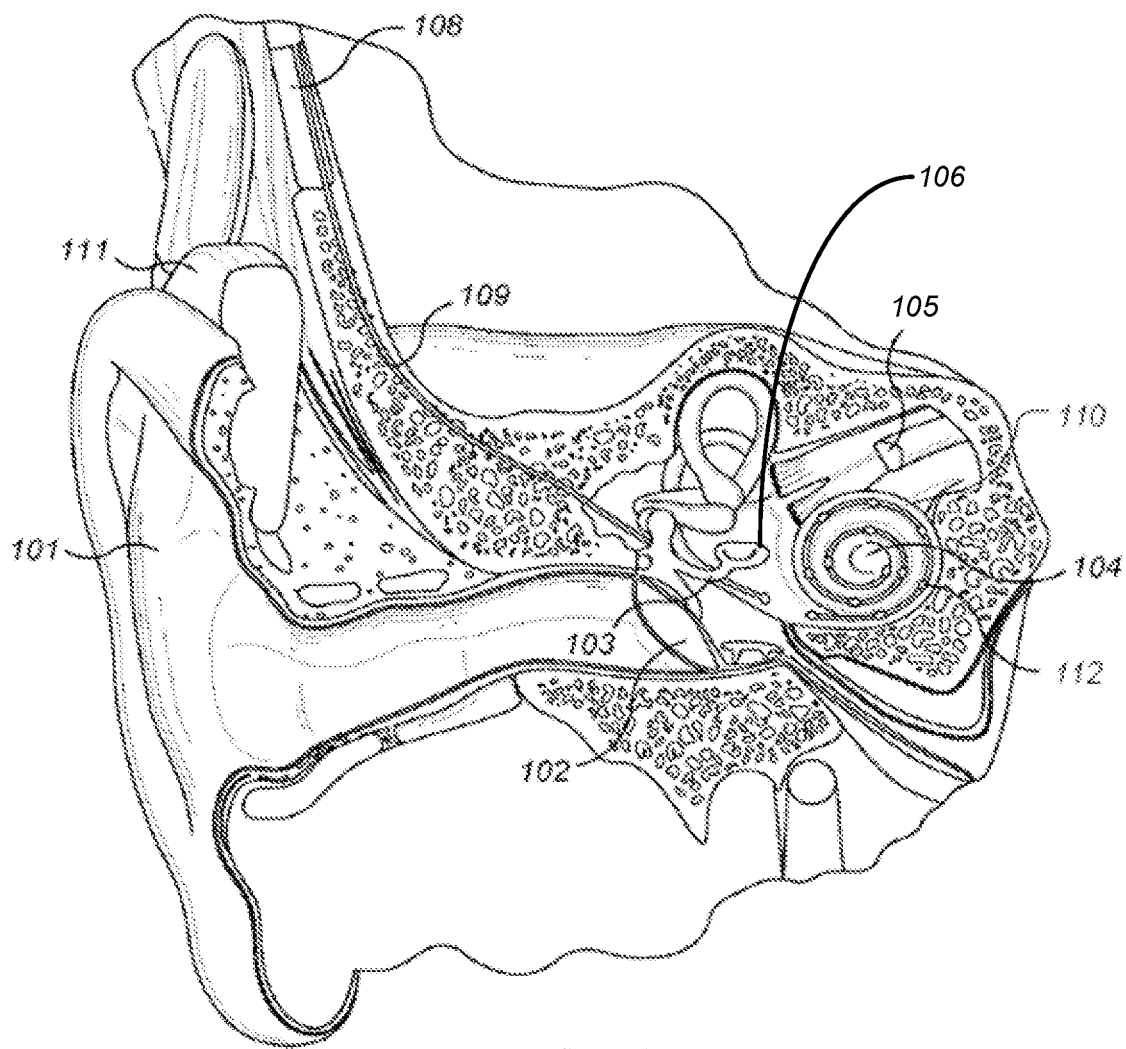
FIG. 1 shows anatomical structures of a typical human ear with a cochlear implant system.
Figure 2:
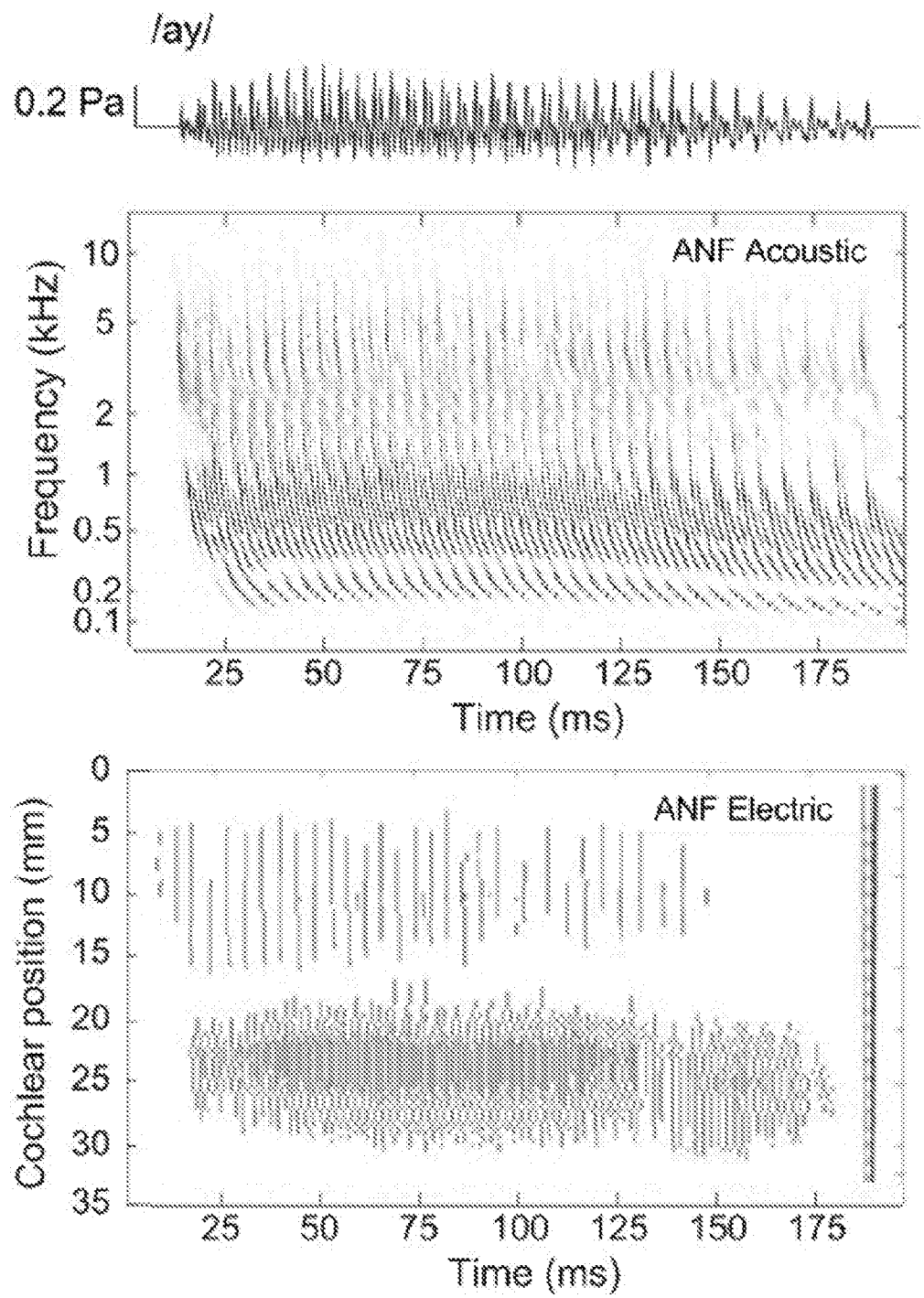
FIG. 2 shows an example of signal processing using the cochlear implant stimulation (CIS) stimulation strategy
Figure 3:
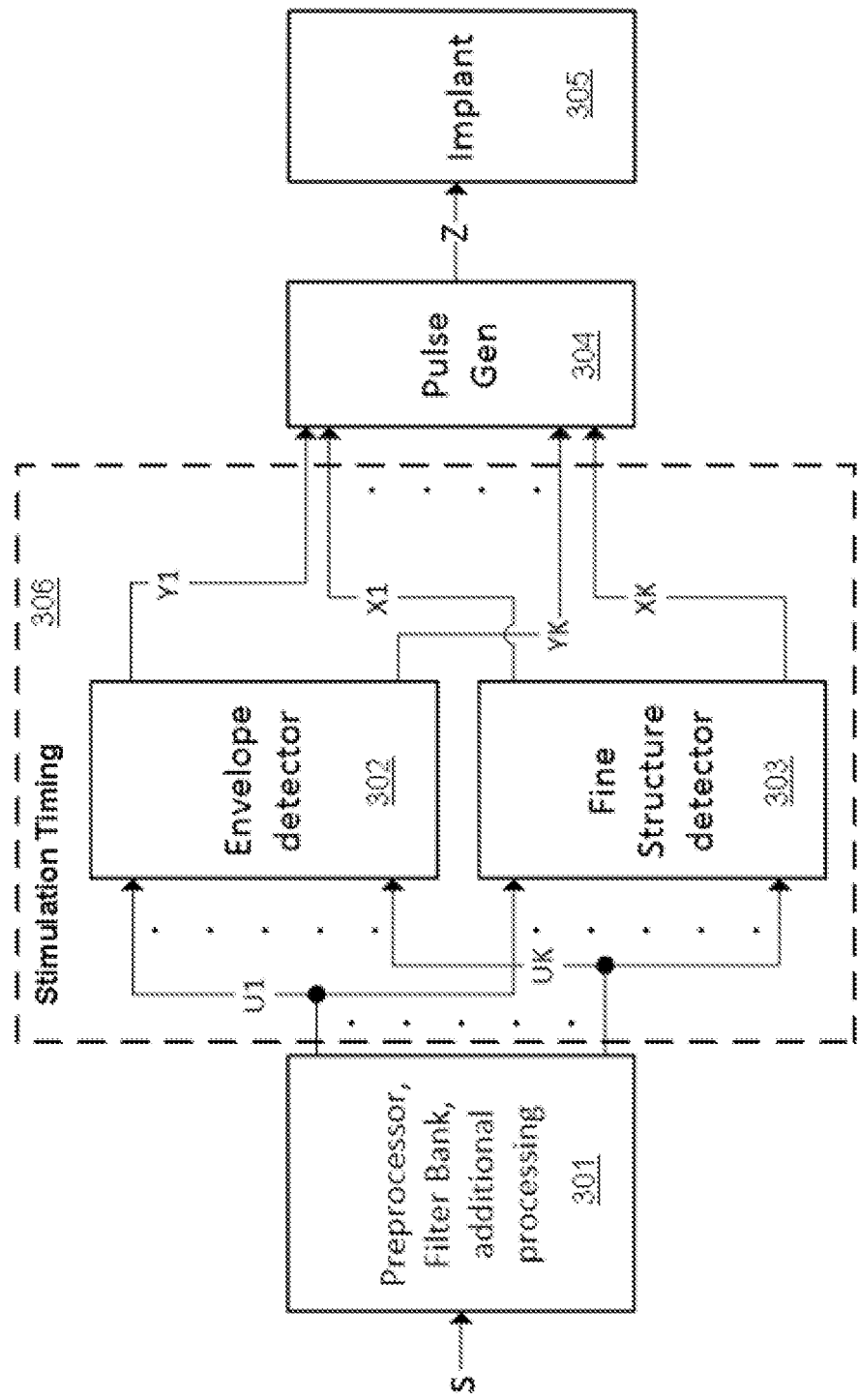
FIG. 3 shows various functional blocks in a signal processing arrangement for a typical cochlear implant system
Figure 4:
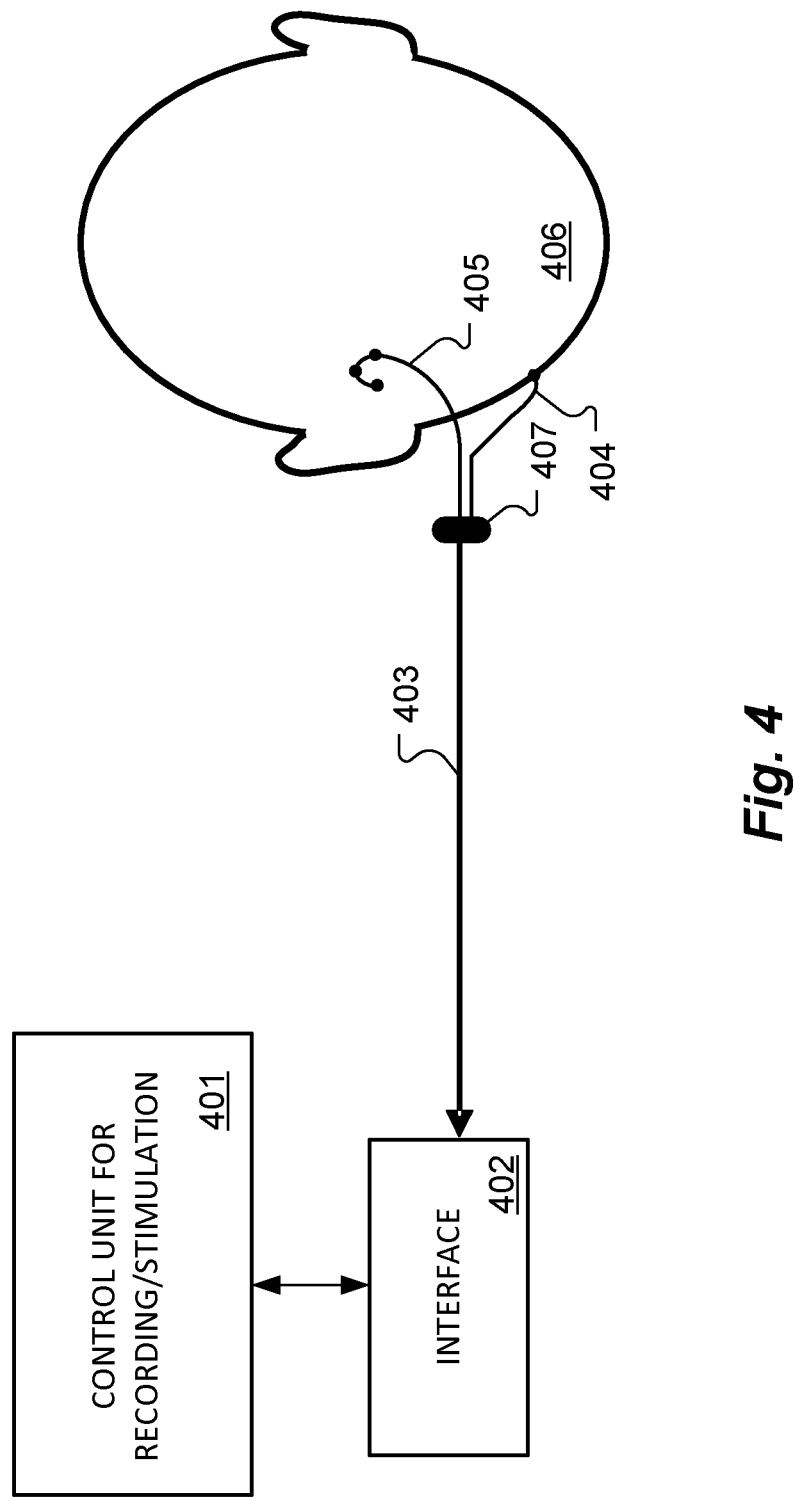
FIG. 4 shows a block diagram of a cochlear implant fitting system according to one specific embodiment of the present invention.

FIG. 4 shows a block diagram of a cochlear implant fitting system according to an embodiment of the present invention. Control Unit 401 for Recording and Stimulation, for example, a Med-El Maestro Cochlear Implant (CI) system, generates stimulation signals and analyzes response measurements. Connected to the Control Unit 401 is an Interface Box 402, for example, a Diagnostic Interface System such as the DIB II conventionally used with the Maestro CI system that formats and distributes the input and output signals between the Control Unit 401 and the system components implanted in the Patient 406. For example, as shown in FIG. 4, there may be an Interface Lead 403 connected at one end to the Interface Box 402 and at the other end having Electrode Plug 407 that then divides into a Cochlear Implant Electrode 404 and an Extra-Cochlear Ground Electrode 405. After delivering a stimulation pulse, a Cochlear Implant Electrode 404 may be used as a sensing element to determine current and voltage characteristics of the adjacent tissue.

Figure 5:
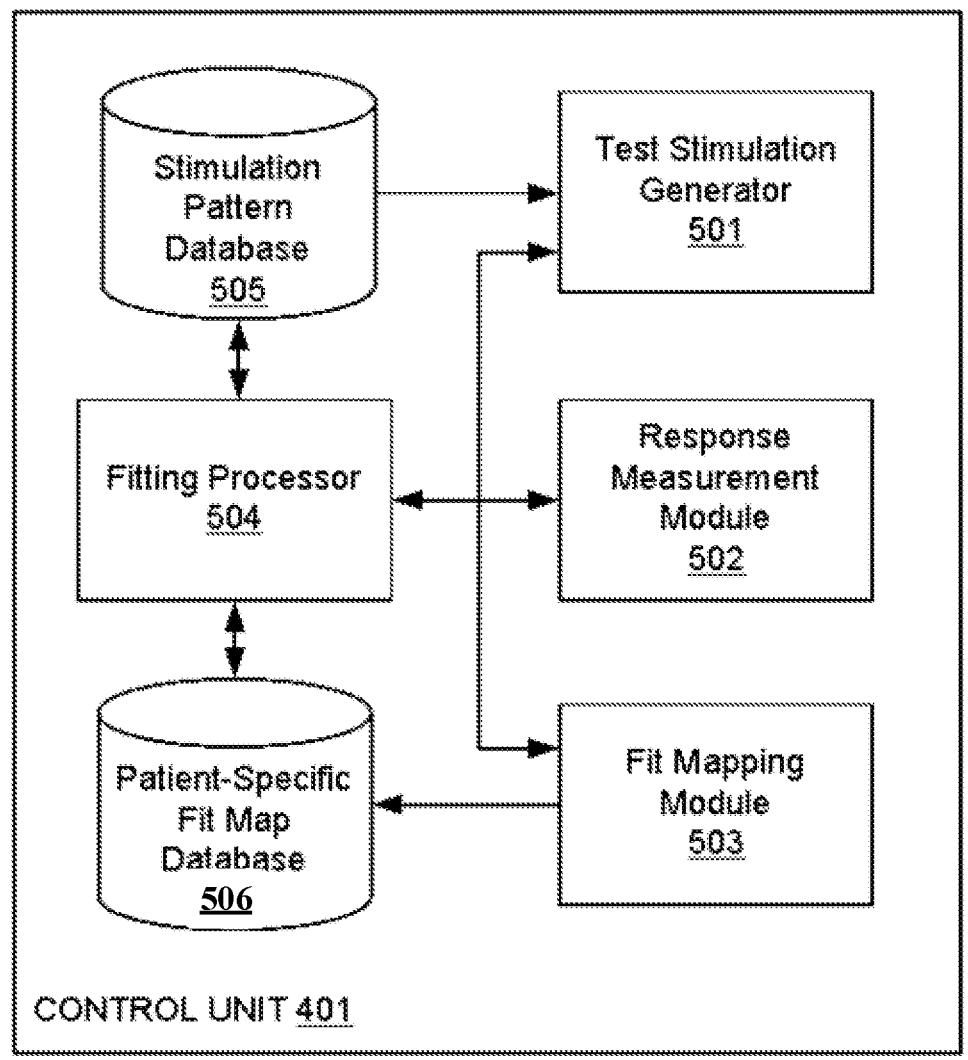
FIG. 5 shows various functional blocks within the fitting system according to an embodiment of the present invention.

The Control Unit 401 is configured as shown in FIG. 5 to for fitting electrode contacts of an implanted cochlear implant electrode array 405. A fitting processor 504 includes at least one hardware implanted processor device and is controlled by software instructions to perform the fitting process, including instructing a test stimulation generator 501 to deliver to at least one of the electrode contacts a test stimulation sequence from a stimulation pattern database 505 which is at a variable charge level and a variable stimulation rate over time where the charge level and stimulation rate are inversely related as a function of a defined loudness percept by the implanted patient to the test stimulation sequence; for example, the defined loudness percept may specifically be a patient-specific Maximum Comfortable Loudness (MCL). The test stimulation generator 501 more specifically may be configured to deliver test stimulation sequences to fit multiple electrode contacts; for example, each of the electrode contacts in the implanted electrode array. This all is described in fuller detail below.

The fitting processor 504 then executes further instructions to cause a response measurement module 502 to obtain objective response measurements—e.g., $ECAP_{thrs}$ measurements—of auditory neural tissues of the implanted patient that are affected by the test stimulation sequence. The fitting processor 504 also executes instructions to cause a fit mapping module 503 to define a patient-specific fit map for the electrode contacts of cochlear implant electrode array based on the objective response measurements, storing the defined fit map in a patient-specific fit map database 505 to be used for subsequent fit adaptation of the cochlear implant system.

More specifically with respect to operation of the test stimulation generator 501, it is known that the perceived loudness of electrical stimuli depends mainly on the charge level and stimulus rate. In general, a higher stimulus rate leads to greater perceived loudness. In the case of ECAP measurements, a charge sweep typically is performed at a fixed stimulation rate, usually at stimulus rates ≤100 pps so as to avoid refractory effects. For given amplitude stimulus, a low stimulus rate reduces the risk of exceeding MCL, but the measurement time is prolonged. Embodiments of the present invention use a dynamically varying stimulus rate to realize an optimal trade-off between fitting time and controlling the risk of exceeding MCL—at low charge levels, a high stimulus rate (e.g. 100 pps), and at high charge levels, a low rate (e.g. 10 pps) is used.

Thus, the function of a defined loudness percept used by the test stimulation generator 501 may represent a scaled product of an exponential charge amplitude factor and an exponential stimulus rate factor. More specifically, electric loudness L can be modelled by:

$$L = k*(A-A_{min})^{Eamp} * R^{Erate}$$

where k is a scaling factor, A defines the stimuli charge, Amin the minimum audible charge level, Eamp is the amplitude exponent, R the stimulus rate, and Erate is the rate exponent. Experiments described in Fu et al., "Effects of noise and spectral resolution on vowel and consonant recognition: Acoustic and electric hearing." *The Journal of the Acoustical Society of America* 104.6 (1998): 3586-3596, which is incorporated herein by reference in its entirety, determined that Eamp=2.72. So:

$$L = k*(A-A_{min})^{2.72} * R^{Erate}$$

Typical stimulus charge level values for THR ($A1000_{min}$) and MCL (A1000) at 1000 pps are 2 nC and 20 nC respectively. For a 100 pps stimulus, THR ($A100_{min}$) and MCL (A100) are 2.3 and 23 nC, respectively. By using:

$$L = k*(A1000 - A1000_{min})^{2.72} * R^{Erate} = k*(A100 - A100_{min})^{2.72} * R^{Erate}$$

$$L = k*18^{2.72}*1000^{Erate} = k*20.7^{2.72}*100^{Erate}$$

$$\left(\frac{18}{20.7}\right)^{2.72} = \left(\frac{1}{10}\right)^{Erate}$$

which leads to:

$$Erate = 2.72 * \frac{\log\left(\frac{18}{20.7}\right)}{\log\left(\frac{1}{10}\right)} = 0.1651$$

$$L = k*(A - A_{min})^{2.72} * R^{0.1651}$$

The rate exponent Erate is roughly 16 times smaller than the charge amplitude exponent Eamp. In ECAP measurements, A−Amin goes up to 18 nC and the stimulus rate R can go up to 100 pps (if refractory states will be avoided). This means that by reducing the stimulus rate R down to 5 pps (for example), the resulting loudness can be reduced by about 40%. But if this low stimulus rate is used in the response measurements, the measurement duration would twenty times longer. To overcome this issue, the stimulus rate can be varied during the ECAP response measurements. For example, at first the maximum loudness Lmax can be calculated for the slowest rate Rmin at largest charge level Amax by:

$$L_{max} = k*(A_{max} - A_{min})^{2.72} * R_{min}^{0.1651}$$

$$\frac{L_{max}}{k} = (A_{max} - A_{min})^{2.72} * R_{min}^{0.1651}$$

For each specific stimulation charge A, the optimum rate by a given maximum rate Rmax is calculated finally by:

$$R = \min\left(R_{max}, 10^{\frac{\log 10\left(\frac{L_{max}}{k*(A-A_{min})^{2.72}}\right)}{0.1651}}\right)$$

Figure 6:
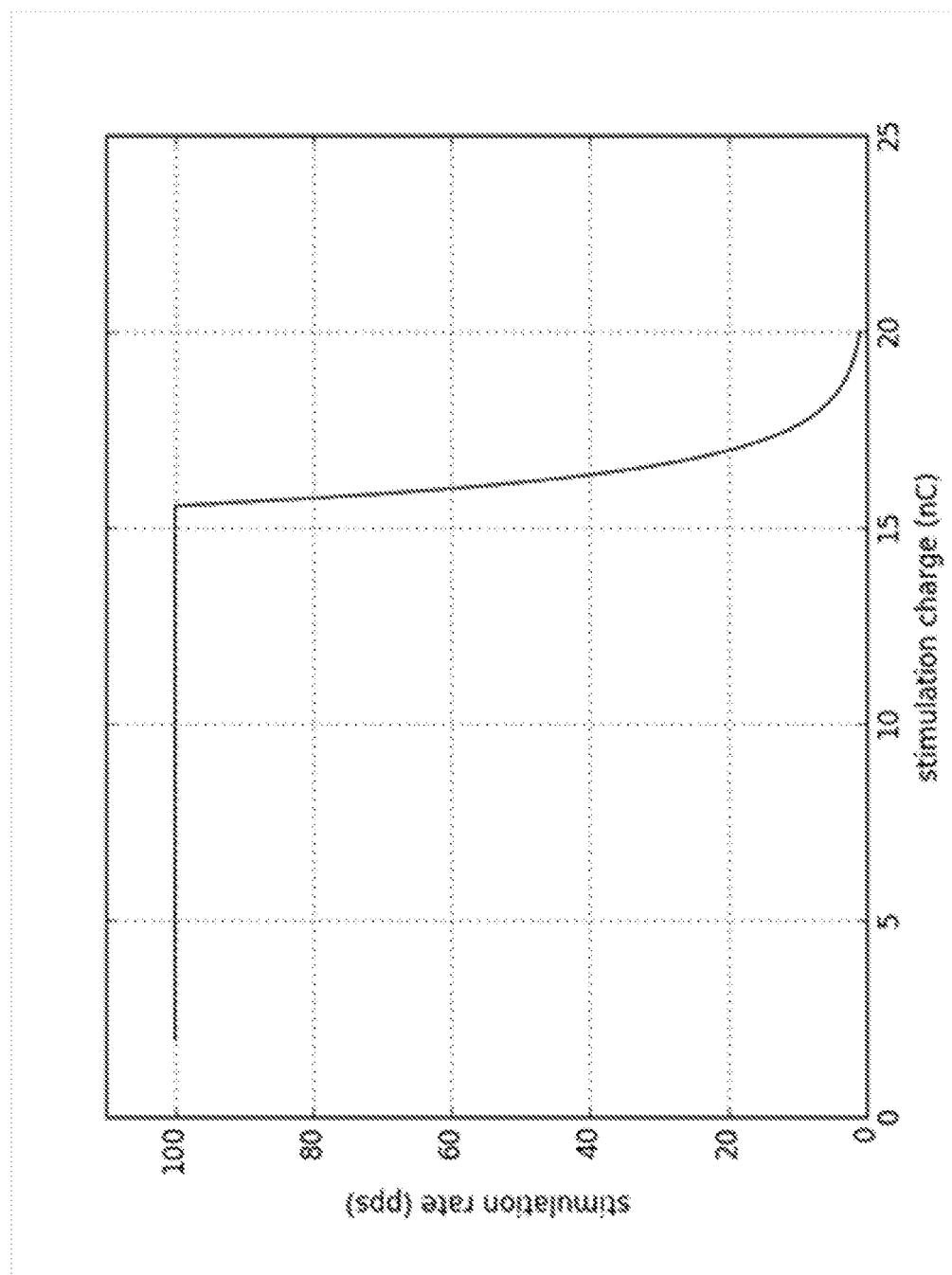
FIG. 6 is a graph of stimulation rate and charge in a fitting arrangement according to an embodiment of the present invention.

As shown in FIG. 6, the maximum stimulus rate is used until reaching a selected charge level, and thereafter the stimulus rate decreases. The perceived loudness stays the same while the stimulation charge is increased. In the given example, the resulting average stimulation rate would be 80.3 pps. Compared to a fix rate of 5 pps, the variable stimulus rate as described above is 16 times faster. In a specific fitting application, population averages can be used to define the variable measurements, i.e. the k scaling parameter.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A fitting system for fitting electrode contacts of a cochlear implant electrode array implanted in a cochlea of an implanted patient, the system comprising:
    a test stimulation generator configured to deliver to at least one of the electrode contacts a test stimulation sequence at a variable charge level and a variable stimulation rate over time, wherein the charge level and stimulation rate are inversely related as a function of a defined loudness percept by the implanted patient to the test stimulation sequence, and wherein the test stimulation sequence is a charge sweep providing increasing charge levels at a maximum stimulus rate until reaching a selected charge level, whereupon the stimulus rate is decreased; and
    a response measurement module configured to obtain objective response measurements of auditory neural tissues of the implanted patient that are affected by the test stimulation sequence; and
    a fit mapping module configured to define a patient-specific fit map for the electrode contacts of cochlear implant electrode array based on the objective response measurements.

2. The system according to claim 1, wherein the response measurement module is configured to obtain objective response measurements that include electrically evoked compound action potential (ECAP) measurements.

3. The system according to claim 2, wherein the response measurement module is configured to obtain ECAP measurements that include ECAP threshold measurements.

4. The system according to claim 1, wherein the defined loudness percept used by the test stimulation generator is based on a patient-specific Maximum Comfortable Loudness (MCL).

5. The system according to claim 1, wherein the function of a defined loudness percept used by the test stimulation generator represents a scaled product of an exponential charge amplitude factor and an exponential stimulus rate factor.

6. The system according to claim 1, wherein the test stimulation generator is configured to deliver a test stimulation sequence to a plurality of the electrode contacts.

7. The system according to claim 1, wherein the test stimulation generator is configured to deliver a test stimulation sequence to each of the electrode contacts.

8. A method of fitting electrode contacts of cochlear implant electrode array implanted in a cochlea of an implanted patient, the method comprising:
    delivering to at least one of the electrode contacts a test stimulation sequence from a test stimulation generator at a variable charge level and a variable stimulation rate over time, wherein the charge level and stimulation rate are inversely related as a function of a defined loudness percept by the implanted patient to the test stimulation sequence, and wherein the test stimulation sequence is a charge sweep providing increasing charge levels at a maximum stimulus rate until reaching a selected charge level, whereupon the stimulus rate is decreased;
    obtaining objective response measurements in a response measurement module of auditory neural tissues of the implanted patient that are affected by the test stimulation sequence; and
    defining a patient-specific fit map for the electrode contacts of cochlear implant electrode array based on the objective response measurements.

9. The method according to claim 8, wherein the objective response measurements include electrically evoked compound action potential (ECAP) measurements.

10. The method according to claim 9, wherein the ECAP measurements include ECAP threshold measurements.

11. The method according to claim 8, wherein the defined loudness percept is based on a patient-specific Maximum Comfortable Loudness (MCL).

12. The method according to claim 8, wherein the function of a defined loudness percept represents a scaled product of an exponential charge amplitude factor and an exponential stimulus rate factor.

13. The method according to claim 8, wherein the test stimulation sequence is delivered to a plurality of the electrode contacts.

14. The method according to claim 8, wherein the test stimulation sequence is delivered to each of the electrode contacts.

15. A cochlear implant system fit to an implanted patient using the fitting method according to any of claim 8.

16. A non-transitory tangible computer-readable medium having instructions thereon for fitting an implanted patient and a hearing implant system having an implanted electrode array with a plurality of electrode contacts, the instructions comprising:
    delivering to at least one of the electrode contacts a test stimulation sequence from a test stimulation generator at a variable charge level and a variable stimulation rate over time, wherein the charge level and stimulation rate are inversely related as a function of a defined loudness percept by the implanted patient to the test stimulation sequence, and wherein the test stimulation sequence is a charge sweep providing increasing charge levels at a maximum stimulus rate until reaching a selected charge level, whereupon the stimulus rate is decreased;
    obtaining objective response measurements in a response measurement module of auditory neural tissues of the implanted patient that are affected by the test stimulation sequence; and
    defining a patient-specific fit map for the electrode contacts of cochlear implant electrode array based on the objective response measurements.

17. The computer-readable medium according to claim 16, wherein objective response measurements include electrically evoked compound action potential (ECAP) measurements.

18. The computer-readable medium according to claim 17, wherein the ECAP measurements include ECAP threshold measurements.

19. The computer-readable medium according to claim 16, wherein the defined loudness percept is based on a patient-specific Maximum Comfortable Loudness (MCL).

20. The computer-readable medium according to claim 16, wherein the function of a defined loudness percept represents a scaled product of an exponential charge amplitude factor and an exponential stimulus rate factor.

21. The computer-readable medium according to claim 16, wherein the test stimulation sequence is delivered to a plurality of the electrode contacts.

22. The computer-readable medium according to claim 16, wherein the test stimulation sequence is delivered to each of the electrode contacts.

* * * * *

UNITED STATES PATENT AND TRADEMARK OFFICE
CERTIFICATE OF CORRECTION

PATENT NO. : 11,077,302 B2
APPLICATION NO. : 16/488815
DATED : August 3, 2021
INVENTOR(S) : Kals Page 1 of 1

It is certified that error appears in the above-identified patent and that said Letters Patent is hereby corrected as shown below:

In the Claims

In Column 10, Line 21:
Replace "to any of claim 8"
With --to claim 8--

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*